United States Patent [19]

Kulle

[11] Patent Number: 4,792,163

[45] Date of Patent: Dec. 20, 1988

[54] SECONDARY LOCK FOR MEDICAL TUBE COUPLING

[75] Inventor: Lee K. Kulle, Mundelein, Ill.

[73] Assignee: Baxter Travenol Laboratories, Inc., Deerfield, Ill.

[21] Appl. No.: 49,751

[22] Filed: May 13, 1987

[51] Int. Cl.$^4$ ............................................. F16L 37/08
[52] U.S. Cl. ..................................... 285/88; 285/81; 285/82; 285/319; 604/93; 604/905
[58] Field of Search ................... 285/82, 87, 88, 81, 285/921, 305, 308, 317, 319, 320; 604/93, 905, 283

[56] References Cited

U.S. PATENT DOCUMENTS

| | | | |
|---|---|---|---|
| 556,174 | 3/1896 | Bateman | 285/317 |
| 579,284 | 3/1897 | Thacker | 285/82 |
| 724,390 | 3/1903 | Hirschell | 285/317 |
| 3,215,456 | 11/1965 | Schmid | 285/87 |
| 4,150,846 | 4/1979 | Fleischer | 285/87 |
| 4,221,449 | 9/1980 | Shugart, Jr. | 339/75 P |
| 4,230,109 | 10/1980 | Geiss | 604/93 |
| 4,270,778 | 6/1981 | Brownell | 285/305 |
| 4,333,505 | 6/1982 | Jones et al. | 604/905 |
| 4,405,163 | 9/1983 | Voges et al. | 285/305 |
| 4,462,654 | 7/1984 | Aiello | 285/921 |

FOREIGN PATENT DOCUMENTS 134562  8/1933  Austria ................. 285/305

Primary Examiner—Randolph A. Reese
Assistant Examiner—Anthony Knight
Attorney, Agent, or Firm—Mary R. Jankousky; Paul C. Flattery; Garrettson Ellis

[57] ABSTRACT

A secondary lock for preventing separation of a pair of connected tubular members comprises an elongated body which carries a toothed rack. A first transversely extending retention member is carried adjacent one end of the body, with a sliding member slidably mounted on the body for longitudinal movement therealong. The sliding member carries a second transversely extending retention member. Each of the retention members are proportioned to grip and retain one of the tubular members. A pawl is provided for engaging the rack to permit the sliding member to be moved toward the first member but not away from the first member. However, the pawl is disengageable to permit the sliding member to be moved away from the first member when desired.

9 Claims, 1 Drawing Sheet

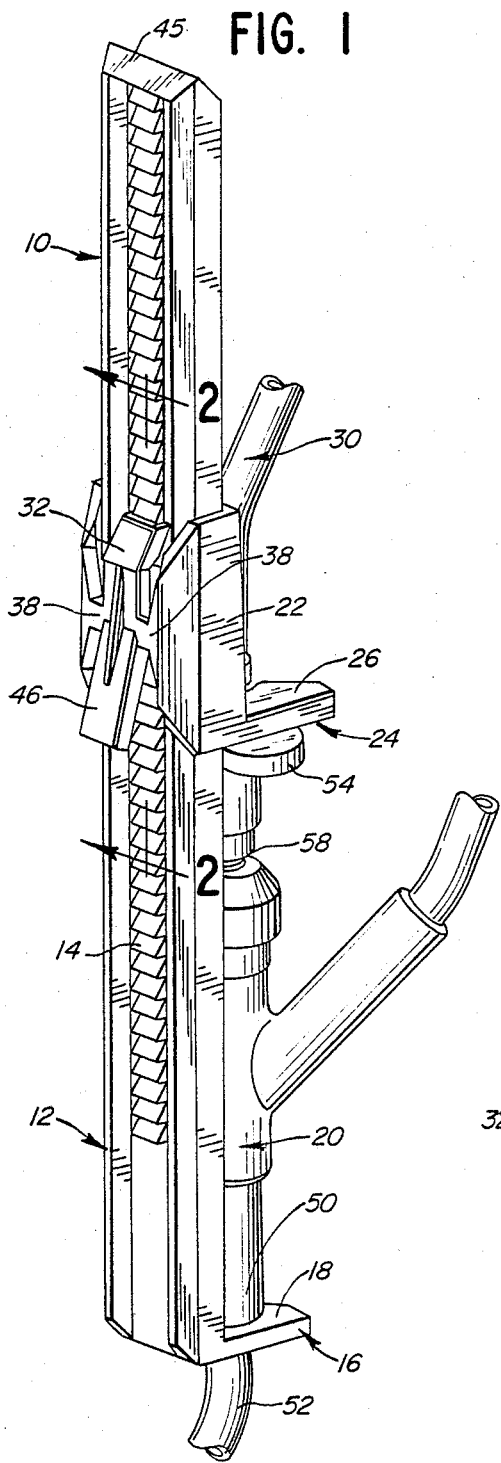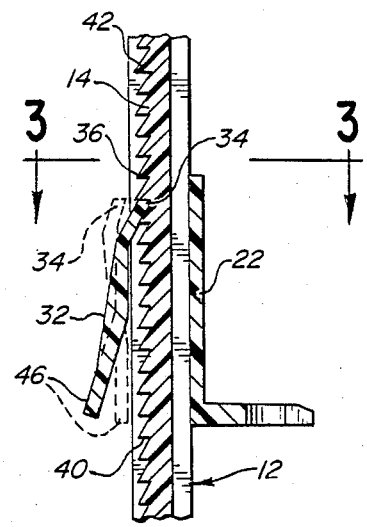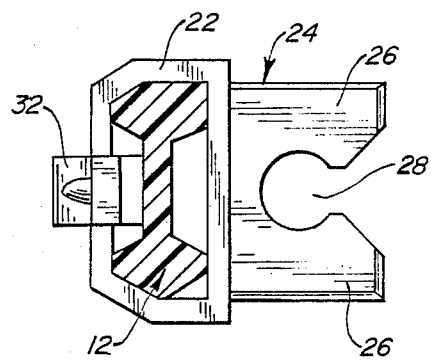

SECONDARY LOCK FOR MEDICAL TUBE COUPLING

TECHNICAL FIELD

Many tubular administration sets for administering medical fluids such as parenteral solutions or blood are in current use. In this use, it is often desired to connect one of such sets with another, for example to add supplemental medications and the like to a stream of parenteral solution being delivered to a patient. Various systems of this type are commercially available.

Often, the various sets to be connected together make their connection through a so-called Luer connection, which is a simple, tapered tube which connects into a correspondingly tapered receptacle. This connection, while simple and easy to make and break, carries with it the hazard that it can accidentally come apart. Such is of course most undesirable in any circumstance, and particularly in the field of medical solution administration sets where sterility is a critical question and the like.

The PiggyMate safety clamp has been marketed by Trend Medical Inc. This device includes a toothed rack having a sliding member carried on it. Both the sliding member and one end of the toothed rack include transversely extending retention members, each of which may be used to grip a connected tubular set member. In the Trend Medical device, the sliding member slides toward the one end which carries the retention member, but the sliding member cannot slide in the other direction. Thus, when the Trend Medical safety clamp has its sliding member advanced, it may not be possible to reuse the device. Similarly, if one by accident slides the sliding member too far forward to effectively grip the particular pair of connected sets, the device is no longer useable since the sliding member cannot be retracted.

In accordance with this invention, a secondary lock is provided for preventing the accidental disconnection of connected, tubular members, particularly medical fluid sets such as sets for parenteral solutions. The device serves as a clamp for holding the respective two sets together, but it is capable of reuse through reopening of the clamping device, in the likely and frequent event that such becomes necessary.

DESCRIPTION OF THE INVENTION

In this invention, a secondary lock is provided for preventing separation of a pair of connected members. The secondary lock comprises an elongated body which carries a toothed rack. A first transversely extending retention member is carried adjacent one end of the body, while a sliding member is slidably mountable on the body for longitudinal movement therealong. The sliding member carries a second transversely extending retention member, each of the retention members being proportioned to grip and retain one of the tubular members of the connected pair described above.

Means are provided for engaging the rack, to permit the sliding member to be moved toward the first member but not away from the first member. However, this engaging means is disengageable to permit the sliding member to be moved away from the first member.

More specifically, the toothed rack preferably comprises individual, spaced teeth which each define a first side facing toward the one end of the body which carries the first transversely extending retention member. This first side of each of the teeth is substantially perpendicular to the body.

A second side of the teeth, facing away from the one end, defines an acute angle to the body which is substantially less than perpendicular. Additionally, the engaging means includes pawl means having a tip for projecting between pairs of the spaced teeth to prevent said motion of the sliding member away from the one end.

Thus, it can be seen that the sliding member can be advanced toward the one end which carries the first retention member, because in so doing the pawl engages and moves over a series of the acutely angled, non-perpendicular second sides of the teeth. However, when one attempts to retract the sliding member, the tip on the end of the pawl engages a generally perpendicular first side of one of the teeth, which effectively prevents retraction of the pawl.

In accordance with this invention, the pawl means is carried on the sliding member by integral, flexible hinge means. As a result of this, the pawl means may be pressed to rotate its tip out from between the pairs of spaced teeth. Additionally, the pawl means is preferably rotationally biased, typically by the integral, flexible hinge means, to place the tip between pairs of spaced teeth. Thus the device functions in the manner described above under normal circumstances. However, it is possible to manually press the pawl out of tooth-engaging relation for a brief moment to retract the sliding member, if and when that is desired.

It is generally preferred for the body to carry, adjacent its end opposed to the one end that carries the first retention member, means which prevent the removal of the sliding member by passing it across the one end. This may simply be an enlarged tooth or rib across which the sliding member cannot pass. The effect of this is to prevent disconnection of the sliding member from the system.

DESCRIPTION OF THE DRAWINGS

FIG. 1 is a perspective view of the secondary lock of this invention shown to be retaining a pair of connected tubular members which constitute parenteral solution sets;

FIG. 2 is a sectional view taken along line 2—2 of FIG. 1; and

FIG. 3 is a sectional view taken along line 3—3 of FIG. 2.

DESCRIPTION OF SPECIFIC EMBODIMENT

Referring to the drawings, the secondary lock 10 of this invention may be made of an integrally molded piece of appropriate plastic, defining a toothed rack 14, plus a first transversely extending retention member 16, made up of a pair of jaws 18, between which there may be retained parenteral solution administration set 20.

Elongated body 12 carries sliding member 22 which is shown to surround rack 14 and to be in substantially slidable relation with it. Slidable member 22 carries a second transversely extending retention member 24 which comprises another pair of jaws 26, defining between them a space 28 to receive another set member 30. The specific functioning and design of jaws 18 may be identical to that of jaws 26, if desired.

Sliding member 22 also defines a pawl 32, which defines a tip 34 which is capable of fitting in between the individual teeth 36 of rack 14 as shown in full lines in FIG. 2. Pawl 32 is shown to be carried on sliding member 22 by a pair of opposed, integral, flexible hinges 38, which connect pawl 32 to the remainder of sliding member 22. The entire sliding member 22 and pawl structure may be integrally molded.

Hinges 38 are proportioned to rotatably bias pawl 32 to place tip 34 of the pawl in between the spaced teeth 36 as shown in FIG. 2. Furthermore, the individual, spaced teeth 36 each define a first side 40 facing toward the one end of body 12 which carries retention member 16. Side 40 can be seen to be substantially perpendicular to body 12.

A second side 42 is defined by each of spaced teeth 36, with second side 42 facing away from the one and which carries retention member 16. This second side 16 defines an acute angle to body 12 which is substantially less than perpendicular, as shown in FIG. 2. Thus, as seen in FIG. 2, it becomes an easy matter to advance sliding member downwardly since, in that circumstance, pawl tip 34 will slide along the acute angled faces 42 to sequentially snap into retaining relation between a series of pairs of teeth 36. However, when one attempts to move sliding member upwardly, pawl tip 34 encounters a generally perpendicular face 40 of a tooth 36, which effectively prevents retraction of the sliding member.

However, in accordance with this invention, pawl 32 defines an outwardly projecting handle 46 on the end of pawl 32 opposed to tip 34. When one depresses handle 46, as shown in phantom lines in FIG. 2, tip 34 of pawl 32 is rotated outwardly, out of engagement between teeth 36. Thus, while end 46 of the pawl is depressed, it becomes possible to retract sliding member 22 upwardly, away from first retention member 16.

A molded bar 45 at the end of body 12 prevents removal of slidable member 22 from body 12.

As shown in FIG. 1, each of jaws 16, 24 rest against an enlarged portion of the respective sets 20, 30, with each enlarged portion being positioned on the inner side of each of the jaws. For jaws 16, enlarged portion 50 may constitute a tubular portion of enlarged diameter in which flexible tubing 52 of set 20 may be held in telescoping relation with respect to flange 16. The enlarged portion 54 may be a widened handle flange of set 30, which is normally used to assist in making connection between set 30 and another set. Because of the presence of these enlargements, in engagement with the apparatus of this invention, the respective sets, 20, 30, cannot retract from their connection with respect to each other at junction area 58, until pawl 34 is rotated to permit retraction of sliding member 22.

The above has been offered for illustrative purposes only, and is not intended to limit the scope of the invention of this application, which is defined in the claims below That which is claimed is:

1. A secondary lock for preventing separation of a pair of connected tubular members, which comprises:
an elongated body which carries a toothed rack; a first transversely extending retention member carried adjacent one end of said body; and a sliding member slideably mounted on said body for longitudinal movement therealong, said sliding member carrying a second transversely extending retention member, each of said retention members being proportioned to grip and retain one of said tubular members; means for engaging said rack to permit said sliding member to be moved toward said first member but not away from said first member, said engaging means being disengageable to permit said sliding member to be moved away from said first member; and said body carrying, adjacent its end opposed to said one end, means preventing the removal of said sliding member by passing it across said opposed end.

2. The secondary lock of claim 1 in which said toothed rack comprises individual, spaced teeth which each define a first side facing towards said one end of the body which is substantially perpendicular to the body, and a second side facing away from said one end which defines an acute angle to said body substantially less than perpendicular; said engaging means including pawl means for projecting between pairs of said spaced teeth to prevent said motion of the sliding member away from said one end.

3. The secondary lock of claim 2 in which said pawl means is carried on said sliding member by integral, flexible hinge means, said pawl means defining a tip positionable between pairs of spaced teeth, whereby said pawl means may be pressed to rotate said tip out from between said pairs of spaced teeth, said pawl means being rotationally biased to place said tip between pairs of spaced teeth.

4. The secondary lock of claim 1 in which each of said retention members comprises a pair of jaws between which a connected tubular member can be placed for retention thereof.

5. The secondary lock of claim 4 in which each of said pairs of jaws carries a connected tubular member portion of a different medical fluid set, a junction between the medical fluid sets being positioned between said pairs of jaws, each of said pairs of jaws resting against an enlarged portion of its carried set on the side of the pair of jaws which faces the other pair of jaws, said enlarged portions being too large to pass between its adjacent pair of jaws.

6. A secondary lock for preventing separation of a pair of connected tubular members, which comprises:
an elongated body which carries a toothed rack; a first transversely extending retention member carried on one end of said body; and a sliding member slidably mounted on said body for longitudinal movement therealong, said sliding member carrying a second transversely extending retention member, each of said retention members being proportioned to grip and retain one of said tubular members, and means for engaging said rack to permit said sliding member to be moved toward said first member but not away from said first member, said engaging means being disengageable to permit said sliding member to be moved away from said first member, in which said toothed rack comprises individual spaced teeth which each define a first side facing towards said one end of the body which is substantially perpendicular to the body, and a second side facing away from said one end which defines an acute angle to said body substantially less than perpendicular; said engaging means including pawl means having a tip for projecting between pairs of said spaced teeth to prevent said motion of the sliding member away from said one end, said body carrying adjacent its end opposed to said one end means preventing removal of said sliding member by passing it across said opposed end.

7. The secondary lock of claim 6 in which said pawl means is carried on said sliding member by integral, flexible hinge means, whereby said pawl means may be pressed to rotate said tip out from between said pairs of spaced teeth, said pawl means being rotationally biased to place said tip between pairs of spaced teeth.

8. The secondary lock of claim 7 in which each of said retention members comprises a pair of jaws between which a connected tubular member can be placed for retention thereof.

9. The secondary lock of claim 8 in which each of said pairs of jaws carries a connected tubular member portion of a different medical fluid set, a junction between the medical fluid sets being positioned between said pairs of jaws, each of said pairs of jaws resting against an enlarged portion of its carried set on the side of the pair of the jaws which faces the other pair of jaws, said enlarged portions being too large to pass between its adjacent pair of jaws.

* * * * *